(12) United States Patent
Steien et al.

(10) Patent No.: US 6,245,292 B1
(45) Date of Patent: *Jun. 12, 2001

(54) METHOD FOR CLEANING INSTRUMENTS WITHIN DENTAL CARE AND SURGERY

(76) Inventors: Jostein Steien, Kapellplatsen 3, S-411 31 Göteborg; Göran Palmers, Hållstamsvägen 35, S-436 39 Askim, both of (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,417

(22) Filed: Jun. 24, 1997

Related U.S. Application Data

(63) Continuation of application No. PCT/SE95/01589, filed on Dec. 27, 1995.

(30) Foreign Application Priority Data

Dec. 28, 1994 (SE) .................................................. 9404551

(51) Int. Cl.$^7$ ...................................................... A61L 2/025
(52) U.S. Cl. .................................. 422/20; 422/26; 134/1; 134/29; 134/30
(58) Field of Search ................................. 422/20, 22, 26, 422/292, 300; 134/95.1, 29, 30, 1, 170

(56) References Cited

U.S. PATENT DOCUMENTS

| | | | |
|---|---|---|---|
| 3,837,805 | * 9/1974 | Boucher | 422/301 |
| 4,710,233 | * 12/1987 | Hohmann et al. | 134/1 |
| 5,288,467 | * 2/1994 | Biermaier | 422/297 |
| 5,380,369 | * 1/1995 | Steinhauser et al. | 134/1 |
| 5,403,555 | * 4/1995 | Steinhauser et al. | 134/1 |
| 5,505,218 | * 4/1996 | Steinhauser et al. | 134/170 |
| 5,571,488 | * 11/1996 | Beerstecher et al. | 422/300 |
| 5,723,090 | * 3/1998 | Beerstecher et al. | 422/300 |

FOREIGN PATENT DOCUMENTS

| | | |
|---|---|---|
| 3324939 | 1/1985 | (DE) . |
| 679406-A1 | * 2/1995 | (EP) . |
| 947700 | 1/1964 | (GB) . |
| 2162424 | 2/1986 | (GB) . |

\* cited by examiner

*Primary Examiner*—Elizabeth McKane
(74) *Attorney, Agent, or Firm*—Merchant & Gould P.C.

(57) ABSTRACT

The invention refers to a method for cleaning and sterilizing instruments within dental care, and incorporating the following partial steps, separately partly known in themselves, a) that the instrument, which is to be cleaned and sterilized is positioned in a treatment chamber, which is closed, b) that the instrument in the treatment chamber is washed with a washing medium, thus that all organic material in the form of internal, as well as any external deposits and coatings are removed, c) that the washing medium is discharged, d) that the instrument is sterilized during a time, which is short as compared to conventional sterilization, e) that the instrument is brought to take up a temperature appropriate for use, and f) that the instrument is lubricated if so needed, whereupon the instrument is ready for removal from treatment chamber for use.

9 Claims, No Drawings

METHOD FOR CLEANING INSTRUMENTS WITHIN DENTAL CARE AND SURGERY

This is a continuation of PCT/SE95/01589 application filed Dec. 27, 1995.

The present invention refers to a method for complete cleaning of different types of instruments, which are used within dental care and surgery, and where the purpose is to interrupt the infection chain.

Within dental care there occurs a number of instruments and aids, which are reused several times, and thus will be used for care of different patients. This of course means, that from hygiene reasons, and in order to reduce to a minimum or rather eliminate the risk of infections, these instruments or aids are cleaned as much as possible between each occasion of use on different patients.

Today the essential cleaning is carried through by sterilization under vacuum, which is effected in autoclave at a rather high temperature, typically about 135° C. Today's autoclaving process is carried through under periods of times of about 12 to 30 minutes, and is well suited e.g. for instrument trays, several surgery instruments, etcetera.

The handpieces and contra-angle handpieces are used within dental care and surgery as carriers for different types of drills, cutters and smoothing discs etcetera. However in their internal air-powered turbines, they have, inter alia rubber details and temperature sensitive metal alloys, which will be negatively influenced at repeated and tedious exposure to the high temperature which is used, whereby the service life will be reduced to about 250 autoclaving cycles, which is an unacceptable low level in view of the fact that the high-tech instruments concerned are rather expensive. At the end of the autoclaving process the instruments have substantially the temperature, at which the autoclaving is carried out, i.e. commonly about 135° C., which means that the instruments must have time to get cooler or cool off before they are can be used again, which may take about 20 minutes.

Regarding handpieces and contra-angle handpieces it furthermore is so that there today are big problems to clean these instruments before the sterilization. In the interior of these instruments there are thus baked aggregations of oil, bacteria, rests of mucous membranes and blood cells, which last-mentioned, inter alia due to the back suction, which is generated when the air turbine is shut down, will be sucked in and admixed with the lubricating oil to form difficult to resolve deposits in different recesses, e.g. on the turbine blade wheel of the handpiece or contra-angle handpiece. These deposits can be carrier of virus and germs, which means an apparent risk of infections. With the technique of today it is hardly possible to effect sterilization or even disinfection of these parts of the instruments.

The purpose of the present invention is to provide a method by means of which it is obtain a uniform process, which allows that the infection chain is interrupted, and this has been obtained by means of the features defined in the accompanying claim 1.

The invention hereinafter will be further described by way of an example.

At the method according to the invention one instrument or a small group of instruments, to be treated, is first positioned in a treatment chamber, which preferably may be one of several to a central unit connected and by the central unit serviced treatment chambers. Hereby it should be noticed that these instruments can be both such, which are made in one piece, such as endoscopes within surgery and within dental care, e.g. lancets and tweezers, tongs, etcetera, and handpieces and contra-angle handpieces having internal channels, which incorporate delicate gaskets and rotatable elements, such as air turbine wheels.

Hereinafter will be described the different partial moments of the method for treating of a contra-angle handpiece, but the handling of other instruments, which are encompassed by the present invention does not differ from what has been described.

As the instrument in this case consists of a contra-angle handpiece, which is provided with an internal rotatable elements, i.e. air turbine wheel, these rotatable parts are braked, in the most simple case in that their rotation is prevented completely, or in that they are prevented from rotating freely under influence of different treatment media, thus that these media will get a mechanical treatment effect against the rotatable parts.

As the contra-angle handpiece has been positioned in the treatment chamber this is closed and locked. Thereupon a drainage opening present in the upper part of the chamber is opened, at the same time as a washing medium, preferably water with detergent added, is introduced in the treatment chamber and at one hand is caused to flow through the hollow interior of the contra-angle handpiece and on the other hand is sprayed onto its outer side. After filling of this dishwater thus that the entire contra-angle handpiece is below the surface ultra-sound is applied, and this ultra-sound aided cleaning sequence is allowed to last for about 1 minute.

After the cleaning process thus carried through the dishwater is discharged from the treatment chamber. This discharge is preferably carried out with aid of pressurized air.

The contra-angle handpiece thus cleaned is thereupon rinsed with fresh water, internally as well as externally. The rinsing water is drained directly and by applying a vacuum all water is removed, preferably also together with the air, which eliminates the risk for air pockets, which can prevent the subsequent treatment from effectively reaching all parts of the instrument, and particularly its hollow portions.

After this sequence the proper sterilization is started, whereby water steam having a temperature of at least 115° C., and preferably 130° C.±5° C. is introduced in the chamber. An appropriate steam pressure has proved itself to be 3,1 bar, and as the pressure in the chamber has reached this level a discharge valve is opened a short while for letting out condensate from the contra-angle handpiece and from the chamber. It furthermore has proven itself appropriate to apply vacuum and supply steam alternately in the chamber, which seems to give a further mechanical treatment, and which is performed during shorter periods of time under an overall sterilization time of about 4 minutes, i.e. a substantially shorter time than the sterilization times earlier used.

After concluded sterilization the pressure in the chamber is lowered by means of vacuum to about 20 millibar.

Thereupon the contra-angle handpiece is brought to resume a temperature appropriate for use, by means of active cooling, which preferably can be effected in that a gas, such as air is allowed to expand under flow through the chamber and the contra-angle handpiece. An appropriate temperature is about 35° C. When the contra-angle handpiece has reached this temperature an oil mist is blown through its hollow portions for lubricating of bearings and turbine. In case the instrument has no internal cavities or rotatable elements this lubricating sequence is of course excluded.

The process is now concluded and the contra-angle handpiece is ready to be removed from the treatment chamber in sterile condition for direct use. The entire process will take about 8 minutes.

The invention is not limited to the procedure described above but modifications and variants are possible within the scope of the appended claims.

Thus it is possible to use instead of vacuum, e.g. ozone, which has a strongly bactericidal effect.

What is claimed is:

1. A method for cleaning and sterilizing instruments within dental care, comprising a combination of the following method steps:
   a) positioning the instrument, which is to be cleaned and sterilized, in a closed treatment chamber,
   b) washing the instrument in the treatment chamber with a washing medium in the form of water with an additive of detergent, thus that all organic material in the form of internal as well as external deposits and coatings are removed, whereby the washing is carried out under simultaneous influence of ultra-sound,
   c) discharging the washing medium by means of pressurized air,
   d) steam-sterilizing the instrument, and applying repeated alternating cycles of vacuum and steam,
   e) drying and cooling the instrument to a temperature appropriate for use by means of a vacuum influence causing water condensed during the sterilization to boil away, thereby taking boiling energy from the instrument, and
   f) lubricating the instrument after drying, whereupon the instrument is ready for removal from the treatment chamber for use.

2. A method as claimed in claim 1, wherein sterilizing the instrument is carried out in an adequate treatment environment, at a temperature of at least 115° C.

3. A method as claimed in claim 2, comprising carrying out treatment with heating and subsequent vacuum suction.

4. A method as claimed in claim 3, comprising sterilizing for a time of about four minutes.

5. A method as claimed in claim 1, wherein cooling of the instrument is effected by causing a gas, which has been caused to expand, to pass through the chamber and the instrument.

6. A method as claimed in claim 1, wherein lubrication of the instrument comprises oil mist lubrication.

7. A method according to claim 6, comprising supplying oil in immediate connection to the instrument.

8. A method as claimed in claim 1, further comprising flowing treatment media through openings or cavities in the instrument, whereby oil is transported via its own conduit.

9. A method as claimed in claim 1, further comprising actively braking rotatable parts of the instrument rotating under influence of treatment media.

* * * * *